United States Patent [19]

Devlin et al.

[11] 3,987,186

[45] Oct. 19, 1976

[54] 2-CARBOXY-4-OXO-4H,6H-(2)-BENZOPYRANO-(3,4-f)-(1)-BENZOPYRANS AND ESTERS AND SALTS THEREOF

[75] Inventors: John P. Devlin, Pierrefonds; Patrick Brian Stewart, St. Andrews East; Kurt Freter, Beaconsfield, all of Canada

[73] Assignee: Boehringer Ingelheim GmbH, Ingelheim am Rhein, Germany

[22] Filed: Feb. 7, 1975

[21] Appl. No.: 548,033

[30] Foreign Application Priority Data

Feb. 18, 1974 Germany............................ 2407631

[52] U.S. Cl............................. 424/283; 260/345.3; 260/293.58; 260/295 A
[51] Int. Cl.² ........................................ A61K 31/35
[58] Field of Search................ 424/283; 260/345.3

[56] References Cited
UNITED STATES PATENTS 3,902,925  8/1975  Devlin et al. .................. 260/345.3

OTHER PUBLICATIONS

Parekh et al., Aust. J. Chem., 23(2), pp. 407–412 (1970).

Primary Examiner—James O. Thomas, Jr.
Assistant Examiner—G. Breitenstein
Attorney, Agent, or Firm—Hammond & Littell

[57] ABSTRACT

Compounds of the formula

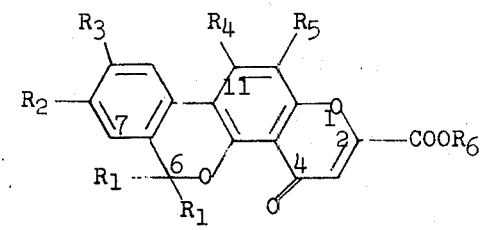

wherein the
$R_1$'s are hydrogen, alkyl of 1 to 3 carbon atoms or together a double-bonded oxygen,
$R_2$ is hydrogen, fluorine, chlorine, methyl, hydroxyl, methoxy, hydroxy-ethoxy, nitro or $-SO_3H$,
$R_3$ is hydrogen, fluorine, chlorine or methoxy,
$R_4$ is hydrogen, methyl or methoxy,
$R_5$ is hydrogen, fluorine, chlorine or methyl, and
$R_6$ is hydrogen or alkyl of 1 to 8 carbon atoms, and, when $R_6$ is hydrogen, salts thereof formed with an inorganic or organic base; the compounds as well as the salts are useful as antiallergics.

4 Claims, No Drawings

2-CARBOXY-4-OXO-4H,6H-(2)-BENZOPYRANO-(3,4-f)-(1)-BENZOPYRANS AND ESTERS AND SALTS THEREOF

This invention relates to novel 2-carboxy-4-oxo-4H, 6H-[2]-benzopyrano-[3,4-f]-[1]-benzopyrans and esters and salts thereof, as well as to methods of preparing these compounds.

More particularly, the present invention relates to a novel class of benzopyrano-benzopyrans represented by the formula

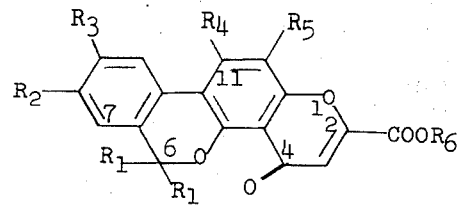

(I)

wherein the
$R_1$'s are hydrogen, alkyl of 1 to 3 carbon atoms or together a double-bonded oxygen,
$R_2$ is hydrogen, fluorine, chlorine, methyl, hydroxyl, methoxy, hydroxy-ethoxy, nitro or —$SO_3H$,
$R_3$ is hydrogen, fluorine, chlorine or methoxy,
$R_4$ is hydrogen, methyl or methoxy,
$R_5$ is hydrogen, fluorine, chlorine or methyl, and
$R_6$ is hydrogen or alkyl of 1 to 8 carbon atoms, and, when $R_6$ is hydrogen, salts thereof formed with an inorganic or organic base.

The compounds embraced by formula I may be prepared by the following methods:

Method A

By subjecting an o-hydroxy-acetophenone of the formula

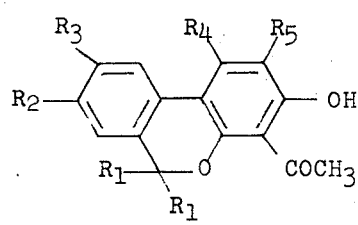

(II)

wherein $R_1$ through $R_5$ have the same meanings as in formula I, to a ring closure reaction with an oxalic acid ester, especially a di-lower alkyl oxalate.

The reaction is preferably carried out in a basic, non-aqueous medium, such as sodium alcoholate. The reactants are advantageously first dissolved or suspended in a nonaqueous solvent, such as ethanol, and the solution or suspension is introduced into the basic medium at room temperature or while gently warming. The reaction mixture is then refluxed for some time, and, after cooling to room temperature, the raw condensation product is acidified, the solution is extracted, the solvent is evaporated, and the residue is heated in a mixture of acetic acid and a concentrated mineral acid.

Method B

By subjecting a fumaric acid ether of the formula

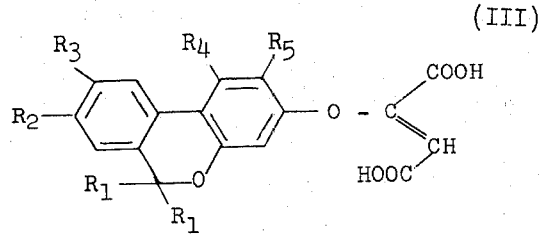

(III)

wherein $R_1$ through $R_5$ have the same meanings as in formula I, to a ring closure reaction with a strong mineral acid.

In general, the starting compound of the formula III is not isolated for use in this method. Instead, a solution thereof is prepared by reacting a 3-hydroxy-6H-dibenzo-[b,d]-pyran of the formula

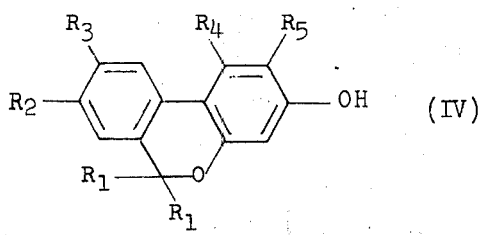

(IV)

wherein $R_1$ through $R_5$ have the same meanings as in formula I, with a dialkylester of acetylene-dicarboxylic acid in a strongly basic medium. For this purpose the dibenzopyran of the formula IV is provided either in solution in an organic solvent, such as dioxane, tetrahydrofuran, dimethylformamide or a lower alkanol, or, if no separate solvent is used, in an excess of the acetylene-dicarboxylic acid ester, and a strong basic compound, such as a quaternary organic base, is added. In most instances it is of advantage to heat the reaction mixture.

After cooling, the intermediate product of the formula III thus formed in the reaction mixture is treated in situ, preferably under anhydrous conditions, with a suitable cyclizing agent, such as concentrated sulfuric acid, chlorosulfonic acid, phosphoric acid or polyphosphoric acid (PPA), and the reaction mixture is then worked up in conventional manner to isolate the desired end product of the formula I. It is often sufficient merely to heat the intermediate product in an anhydrous aprotic solvent to initiate the ring closure.

If it is desired to isolate the intermediate product of the formula III, the reaction mixture formed in the manner described above by reaction of a 3-hydroxy-6H-dibenzo-[b,d]-pyran of the formula IV with a diester of acetylene-dicarboxylic acid is, after treatment with an alkali and acidification, filtered and the filter cake is washed and recrystallized in the usual manner.

A free acid of the formula I ($R_6 = H$) obtained as the desired end product in methods A and B may, if desired, be converted into a salt thereof with an inorganic or organic base. Examples of bases suitable for salt formation are alkali metal hydroxides, carbonates or bicarbonates; alkaline earth metal hydroxides, carbonates or bicarbonates; ammonia; mono-, di- or tri-lower alkylamines, such as triethylamine; mono-, di- or tri-lower alkanolamines, such as triethanolamine; and heterocyclic amines, such as piperidine or pyridine. For this purpose the free acid is dissolved or suspended in water, and then the desired base is added to the solution or suspension until it has a pH of 7. The resulting solution of the salt is then preferably freeze-dried, because of the possibility that the salt may decompose if the solution thereof is evaporated.

Furthermore, an ether group present in an end product obtained by means of the above methods may subsequently be split and converted into a hydroxyl group. Likewise, an ester may be converted into the corresponding free acid, or conversely a free acid may be converted into an ester. Moreover, if $R_2$ in formula I is to be nitro or $-SO_3H$, these substituents may subsequently be introduced into an end product of the formula I which is unsubstituted in the 8-position.

The starting compounds of the formula II for method A are accessible, for example, by
a. condensation of an optionally substituted o-bromobenzoic acid with a 2,6-dihydroxy-acetophenone;
b. acetylation of a correspondingly substituted 3-hydroxy-6H-dibenzo-[b,d]-pyran of the formula IV, for instance by means of acetic acid/boron trifluoride; or
c. the Fries Rearrangement [K. Fries et al., Berichte 41, 4271 (1908); and, ibid. 43, 212 (1910)] of the ester obtained by reacting acetic acid anhydride with a phenol (IV) in the presence of aluminum chloride.

A phenol of the formula IV in turn is obtained, when $R_1$ is to be hydrogen, by reduction with diborane-borontrifluoride or, when $R_1$ is to be lower alkyl, by Grignard alkylation of a corresponding lactone of the formula

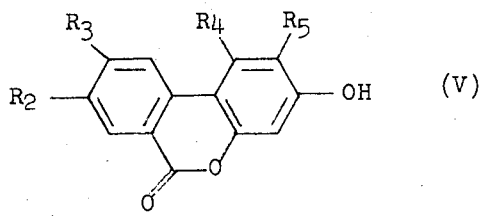

(V)

wherein $R_2$ through $R_5$ have the meanings previously defined.

A lactone of the formula V in turn may be prepared from a correspondingly substituted o-bromo-benzoic acid with the aid of a suitable resorcinol derivative pursuant to the method of W. R. H. Hurtley, J. Chem. Soc. 1929, page 1870.

By means of the above described methods and procedures the following end products of the formula I, for example, can be obtained:

, 2-Carboxy-4-oxo-6,6-dimethyl-11-methoxy-4H,6H-[2]-benzopyrano-[3,4-f]-[1]-benzopyran,
2-Carboxy-4-oxo-6,6-dimethyl-8-methoxy-4H,6H-[2]-benzopyrano -[3,4-f]-[1]-benzopyran,
2-Carboxy-4-oxo-6,6-dimethyl-8-hydroxy-4H,6H-[2]-benzopyrano-[3,4-f]-[1]-benzopyran,
2-Carboxy-4-oxo-6,6-dimethyl-8-hydroxyethoxy-4H,6H-[2]-benzopyrano-[3,4-f]-[1]-benzopyran,
2-Carboxy-4-oxo-6,6,12-trimethyl-4H,6H-[2]-benzopyrano-[3,4-f]-[1]-benzopyran,
2-Carboxy-4-oxo-6,6-dimethyl-8-fluoro-4H,6H-[2]-benzopyrano-[3,4-f]-[1]-benzopyran,
2-Carboxy-4-oxo-6,6-di-n-propyl-4H,6H-[2]-benzopyrano-[3,4-f]-[1]-benzopyran,
2-Carboxy-4-oxo-6,6-dimethyl-8-chloro-4H,6H-[2]-benzopyrano[3,4-f]-[1]-benzopyran,
2-Ethoxycarbonyl-4,6-dioxo-4H,6H-[2]-benzopyrano-[3,4-f]-[1]-benzopyran,
2-Carboxy-4-oxo-6,6-dimethyl-4H,6H-[2]-benzopyrano-[3,4-f]-[1]-benzopyran,
2-Carboxy-4-oxo-6,6,11-trimethyl-4H,6H-[2]-benzopyrano-[3,4-f]-[1]-benzopyran,
2-Carboxy-4-oxo-6,6-dimethyl-9-chloro-4H,6H-[2]-benzopyrano[3,4-f]-[1]-benzopyran,
2-Carboxy-4-oxo-6,6-dimethyl-12-chloro-4H,6H-[2]-benzopyrano[3,4-f]-[1]-benzopyran,
2-n-Butyloxycarbonyl-4-oxo-8-sulfo-12-chloro-4H,6H-[2]-benzopyrano-[3,4-f]-[1]-benzopyran,
2-Carboxy-4-oxo-12-chloro-4H,6H-[2]-benzopyrano-[3,4-f]-[1]-benzopyrane,
2-(n-Butyloxy-carbonyl)-4-oxo-6,6-dimethyl-8-sulfo-12-chloro4H,6H-[2]-benzopyrano-[3,4-f]-[1]-benzopyran,
2-Carboxy-4-oxo-6,6-dimethyl-8-sulfo-12-chloro-4H,6H-[2]-benzopyrano-[3,4-f]-[1]-benzopyran,
2-Carboxy-4-oxo-6,6-dimethyl-8-nitro-12-chloro-4H,6H-[2]-benzopyrano-[3,4-f]-[1]-benzopyran,
2-Carboxy-4-oxo-6,6,12-trimethyl-8-sulfo-4H,6H-[2]-benzopyrano-[3,4-f]-[1]-benzopyran, and
2-(n-Octyloxy-carbonyl)-4-oxo-6,6-dimethyl-8-chloro-4H,6H-[2]-benzopyrano-[3,4-f]-[1]-benzopyran.

The following examples further illustrate the present invention and will enable others skilled in the art to understand it more completely. It should be understood, however, that the invention is not limited solely to the particular examples given below.

EXAMPLE 1

2-Carboxy-4-oxo-6,6-dimethyl-11-methoxy-4H,6H-[2]-benzopyrano-[3,4-f]-[1]-benzopyran by method A A suspension of 223.7 gm (0.75 mol) of 1-methoxy-3-hydroxy-4-acetyl-6,6-dimethyl-6H-dibenzo-[b,d]-pyran in a mixture of 220 gm of diethyl oxalate and 800 ml of ethanol was poured all at once at 40° C into a solution of 69 gm (3 mols) of sodium in 2.3 liters of anhydrous ethanol. The reaction mixture was refluxed for 2 hours, then cooled to 25° C, poured into 3 liters of water, acidified with concentrated hydrochloric acid and extracted three times with 0.5 liter of chloroform. The combined extracts were substantially freed from solvent, and the residue was refluxed for 1 hour in a mixture of 1.57 liters of acetic acid and 0.63 liter of concentrated hydrochloric acid. The mixture thus obtained was stirred into 5 liters of cold water, extracted three times with 1 liter of chloroform, the solvent was evaporated from the combined extracts, and the residue dried. After recrystallization from isopropanol, 220 gm (83% of theory) of the compound of the formula

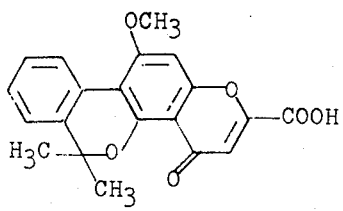

were obtained, which had a melting point of 226°-229° C.

The starting compound was prepared as follows: A mixture of 431 gm (1.68 mols) of 1-methoxy-3-hydroxy-6,6-dimethyl-6H-dibenzo-[b,d]-pyran, 151 gm (2.52 mols) of acetic acid and 4 liters of benzene was saturated, while stirring, with borontrifluoride gas; during this time the temperature rose to 34° C, and the crystals dissolved. After standing for 5 days at room temperature, the reaction mixture was poured into 5 liters of water containing 400 gm of sodium hydroxide, while stirring. The benzene phase was separated, and the aqueous phase extracted three times with benzene. The combined benzene phases were dried over anhydrous sodium sulfate, the solvent was evaporated, and the residue was chromatographed on 6 kg of silicic acid, using chloroform as the eluant. The first fractions contained 1-methoxy-3-hydroxy-4-acetyl-6,6-dimethyl-6H-dibenzo-[b,d]-pyran, which was recrystallized from benzene/light gasoline. Yield: 210 gm (42% of theory), m.p. 89°-90° C.

The ethanolamine salt of 2-carboxy-4-oxo-6,6-dimethyl-11-methoxy-4H,6H-[2]-benzopyrano-[3,4-f]-[1]-benzopyran was prepared by dissolving 249 gm (0.706 mol) of the free acid at about 50° C in a mixture of 2.5 liters of chloroform and 1 liter of methanol. The solution was cooled to 15° C, and 43.5 gm (0.71 mol) of ethanolamine were added dropwise over a period of 30 minutes. Afterwards, the solution was evaporated to about 1 liter, 2 liters of ether were added, and the precipitating crystals were recrystallized three times from a total of 5 liters of methanol/ether. 278 gm (95% of theory) of the ethanolamine salt, m.p. 198°-199° C, were obtained.

EXAMPLE 2

2-Carboxy-4-oxo-6,6-dimethyl-8-methoxy-4H,6H-[2]-benzopyrano -[3,4-f]-[1]-benzopyran by method A A suspension of 7.1 gm (0.024 mol) of 3-hydroxy-4-acetyl-6,6-dimethyl-8-methoxy-6H-dibenzo-[b,d]-pyran in a mixture of 7.3 gm (0.05 mol) of diethyloxalate and 150 ml of ethanol was added all at once to a stirred solution of 4.6 gm (0.2 mol) of sodium in 150 ml of ethanol. The resulting mixture was refluxed for 1 hour and then cooled to room temperature, the precipitated raw reaction product was filtered off, washed with ether, dried and heated for 1 hour in a mixture of 40 ml of acetic acid and 16 ml of concentrated hydrochloric acid. After cooling, the insoluble precipitate was filtered off and recrystallized from methanol, yielding 5.05 gm (60% of theory) of the compound named in the heading, which had a melting point of 250°-251° C.

The ethanolamine salt, m.p. 199°-201° C, was prepared in a manner analogous to that described in Example 1.

The starting compound was prepared as follows: A suspension of 104 gm (0.45 mol) of 2-bromo-5-methoxy-benzoic acid and 45 gm (0.3 mol) of 2,6-dihydroxy-acetophenol in 300 ml of water was admixed, while stirring, with 36 gm (0.9 mol) of sodium hydroxide. The mixture was refluxed for 5 minutes and, after addition of 30 ml of a 10% copper-II-sulfate solution, it was heated for 15 minutes more. Then the mixture was cooled to room temperature, and the precipitate was filtered off, dried and recrystallized from dimethylformamide. 22.5 gm (26.6%) of 3-hydroxy-4-acetyl-6-oxo-8-methoxy-6H-dibenzo-[b,d]-pyran, m.p. 197°-199° C, were obtained.

A suspension of 27.4 gm (0.1 mol) of this compound in 500 ml of benzene was added to a solution of 0.5 mol of methyl magnesium iodide in 200 ml of ether. The mixture was refluxed for 3 hours, cooled and poured into a mixture of 1 kg of ice and 50 ml of concentrated sulfuric acid. The organic phase was separated and dried over sodium sulfate. After filtration, the filtrate was treated for 10 minutes with borontrifluoride, poured into 250 ml of a 2 N sodium hydroxide solution and acidified with 4 N hydrochloric acid. The organic phase was separated, and the aqueous phase extracted three times with 100 ml ether each. The combined extracts were dried, evaporated and chromatographed on silicic acid (eluant: benzene), yielding 7.1 gm (24.7% of theory) of 3-hydroxy-4-acetyl-6,6-dimethyl-8-methoxy-6H-dibenzo-[b,d]pyran, m.p. 103°-104° C.

EXAMPLE 3

2-Carboxy-4-oxo-6,6-dimethyl-8-hydroxy-4H,6H-[2]-benzopyrano[3,4-f]-[1]-benzopyran by method A 2.5 gm (0.007 mol) of 2-carboxy-4-oxo-6,6-dimethyl-8-methoxy-4H,6H-[2]-benzopyrano-[3,4-f]-[1]-benzopyran, prepared as described in Example 2, were refluxed for 4 hours in 50 ml of hydroiodic acid. Then, the reaction mixture was cooled and diluted with 200 ml of water. The precipitated yellow crystals were filtered off, washed with water, dried and recrystallized from methanol. 250 gm (10.5% of theory) of the compound named in the heading, m.p. 256°-258° C, were obtained. The ethanolamine salt, prepared in analogy with Example 1, had a melting point of 200°-202° C.

EXAMPLE 4

2-Carboxy-4-oxo-6,6,12-trimethyl-4H,6H-[2]-benzopyrano[3,4-f]-[1]-benzopyran by method A A suspension of 4.5 gm (0.016 mol) of 2-methyl-3-hydroxy-4-acetyl-6,6-dimethyl-6H-dibenzo-[b,d]-pyran in a mixture of 4.4 gm (0.03 mol) of diethyl oxalate and 100 ml of ethanol was stirred at 50° C all at once into a solution of 3.7 gm (0.16 mol) of sodium in 100 ml of ethanol. The resulting mixture was refluxed for 1 hour, cooled to room temperature, and the precipitated raw reaction product was filtered off, washed with ether, dried and then heated for one hour in a mixture of 40 ml of glacial acetic acid and 16 ml of concentrated hydrochloric acid. Then, the reaction mixture was cooled, filtered and the filter cake was recrystallized from methanol/chloroform. 2.5 gm (47.2% of theory) of the compound named in the heading, m.p. 245°–246° C, were obtained. The ethanolamine salt, prepared in analogy to Example 1, had a melting point of 219°–220° C.

The starting compound was prepared as follows: A mixture of 29.0 gm (0.103 mol) of 2-methyl-3-acetoxy-6,6-dimethyl-6H-dibenzo-[b,d]-pyran, 29 gm (0.22 mol) of aluminum chloride and 250 ml of nitrobenzene was stirred for 2 hours at 5° C. After decomposition of the aluminum chloride with ice water, the solvent was removed by steam distillation, the residue was extracted with ether, the extracts were dried, and the ether was evaporated. After recrystallization of the residue from ether, 4.5 gm (15.3% of theory) of 2-methyl-3-hydroxy-4-acetyl-6,6-dimethyl-6H-dibenzo-[b,d]-pyran, m.p. 123°–125° C, were obtained.

EXAMPLE 5

2-Carboxy-4-oxo-6,6-dimethyl-8-fluoro-4H,6H-[2]-benzopyrano-[3,4-f]-[1]-benzopyran by method A A stirred solution of 1.6 gm (0.07 mol) of sodium in 50 ml of ethanol was admixed all at once with a suspension of 2.2 gm (0.008 mol) of 3-hydroxy-4-acetyl-6,6-dimethyl-8-fluoro-6H-dibenzo-[b,d]-pyran in a mixture of 2.05 gm (0.014 mol) of diethyl oxalate and 50 ml of ethanol. The mixture was refluxed for 1 hour, then cooled to room temperature, and the precipitated raw reaction product was filtered off, washed with ether, dried and heated for 1 hour in a mixture of 12 ml of acetic acid and 5 ml of concentrated hydrochloric acid. After cooling, the reaction mixture was filtered, and the precipitated crystals were recrystallized from methanol, yielding 1.2 gm (45% of theory) of the compound named in the heading, which had a melting point of 268° C (decomp.).

The melting point of its ethanolamine salt, prepared in analogy to Example 1, was 203°–205° C.

The starting compound, m.p. 156°–158° C, was obtained in analogy to the method described in Example 2 from 2-bromo-5-fluoro-benzoic acid and 2,6-dihydroxy-acetophenone via 3-hydroxy-4-acetyl-6-oxo-8-fluoro-6H-dibenzo-[b,d]-pyran, m.p. 223°–225° C.

EXAMPLE 6

2-Carboxy-4-oxo-6,6-dimethyl-12-chloro-4H,6H-[2]-benzopyrano[3,4-f]-[1]-benzopyran by method B A solution of 18 gm (0.07 mol) of 2-chloro-3-hydroxy -6,6-dimethyl-6H-dibenzo-[b,d]-pyran and 11.4 gm (0.08 mol) of dimethyl-acetylene-dicarboxylate in 30 ml of dioxane was admixed with 1 ml of a 40% solution of benzyl trimethylammonium hydroxide in water, and the resulting solution was heated at 80° C for 30 minutes. After cooling, 50 ml of 5 N sodiumhydroxide were added, and the mixture was heated for another hour. Then, the mixture was cooled, acidified with concentrated hydrochloric acid, and the oil formed thereby was extracted with ether, the extracts were dried and evaporated, and concentrated sulfuric acid was slowly added to the residue at room temperature. After standing for one day at room temperature, the resulting solution was poured into ice water, filtered, and the isolated solid product was recrystallized from methanol, yielding 5.8 gm (25% of theory) of the desired end product. Melting point of the ethanolamine salt, obtained in analogy to Example 1: 164°–166° C.

EXAMPLE 7

2-Carboxy-4-oxo-6,6-dimethyl-4H,6H-[2]-benzopyrano-[3,4]-[1]benzopyran by method A A suspension of 600 mgm (2.25 millimols) of 3-hydroxy-4-acetyl-6,6-dimethyl-6H-dibenzo-[b,d]-pyran in a mixture of 600 mgm (4.1 millimols) of diethyl oxalate and 12 ml of ethanol was added at 50° C all at once to a stirred solution of 460 mgm (20 millimols) of sodium in 25 ml of ethanol. The resulting mixture was refluxed for 1 hour, then cooled to room temperature, and the precipitated raw reaction product was isolated, dried and refluxed for one hour in a mixture of 10 ml of acetic acid and 4 ml of concentrated hydrochloric acid. After cooling, the end product was isolated and recrystallized from chloroform/methanol, yielding 200 mgm (35% of theory) of the compound named in the heading, which had a melting point of 217°–218° C.

The starting compound was obtained, in analogy to the method described in Example 2, from o-bromobenzoic acid and 2,6-dihydroxy-acetophenone via 3-hydroxy-4-acetyl-6-oxo-6H-dibenzo-[b,d]-pyran, m.p. 205°–206° C.

EXAMPLE 8

2-Carboxy-4-oxo-6,6-di-n-propyl-4H,6H-[2]-benzopyrano-[3,4-f]-[1]-benzopyran by method A A stirred solution of 3.7 gm (0.16 mol) of sodium in 100 ml of ethanol was admixed at a temperature of 50° C all at once with a solution of 5.0 gm (0.016 mol) of 3-hydroxy-4-acetyl-6,6-di-n-propyl-6H-dibenzo-[b,d]-pyran in a mixture of 4.4 gm (0.03 mol) of diethyl oxalate and 100 ml of ethanol. The resulting mixture was refluxed for 1 hour and was then poured into 500 ml of water containing 5 ml of concentrated hydrochloric acid. The aqueous mixture was extracted with ether, and the extract was dried and evaporated. The residue was heated for 1 hour in a mixture of 40 ml of acetic acid and 16 ml of concentrated hydrochloric acid, cooled and poured into 500 ml of water. The resulting precipitate was filtered off, dried and recrystallized from methanol, yielding 2.4 gm (41% of theory) of the compound named in the heading, which had a melting point of 227°–229° C.

The ethanolamine salt, prepared in analogy to Example 1, had a melting point of 180°–182° C.

The starting compound was prepared as follows: A solution of 0.3 mol of propyl magnesium iodide in 150 ml of ether was admixed all at once with a suspension of 16.6 gm (0.065 mol) of 3-hydroxy-4-acetyl-6-oxo-6H-dibenzo-[b,d]-pyran (prepared analogous to Example 7) in 300 ml of benzene. The resulting mixture was heated for 3 hours and subsequently decomposed by addition of 500 ml of water containing 25 ml of concentrated sulfuric acid. The organic phase was separated, the aqueous phase was extracted with ether, and the combined extracts were dried over sodium sulfate. After evaporation of the solvent, the residue was dissolved in 100 ml of dry benzene, treated for 15 minutes with borontrifluoride, and then poured into 2 N sodium hydroxide. After acidification with 2 N hydrochloric acid, the reaction mixture was extracted with ether, the extract was evaporated, and the residue was chromatographed on silicic acid, yielding 5.0 gm (= 23.5% of theory) of 3-hydroxy-4-acetyl-6,6-di-propyl-6H-dibenzo-[b,d]-pyran, m.p. 83°–83.5° C.

EXAMPLE 9

2-Carboxy-4-oxo-12-chloro-4H,6H-[2]-benzopyrano-[3,4-f]-[1]benzopyran by method B 7.0 gm of 2-chloro-6H-dibenzo-[b,d]-pyranyl-(3)-fumaric acid ether were slowly added at room temperature to concentrated sulfuric acid. After standing for 90 minutes at room temperature the solution was poured into ice water, and the resulting precipitate was filtered off and recrystallized from boiling dimethylformamide. 2.5 gm of the compound named in the heading, which had a melting point of 268°–270° C, were obtained. Its ethanolamine salt, prepared in analogy to Example 1, had a melting point of 210°–211° C.

The starting compound was obtained in the following way: A solution of 9.8 gm (0.04 mol) of 2-chloro-3-hydroxy6H-dibenzo-[b,d]-pyran and 9.0 gm (0.06 mol) of dimethyl acetylene-dicarboxylate in 20 ml of dioxane was admixed with 0.85 ml of a 40% solution of benzyl trimethylammonium hydroxide in water. The resulting solution was heated for 10 minutes at 75° C, then cooled, admixed with 5 N sodium hydroxide, and heated for one hour more. Then, the reaction mixture was cooled, acidified with concentrated hydrochloric acid, and the precipitate formed thereby was filtered off, washed with water, dried and recrystallized from a mixture of acetic acid and chloroform (1:9). The compound named in the heading, m.p. 242°–243° C, was obtained with a yield of 10.5 gm (99%) of theory).

EXAMPLE 10

2-(n-Butoxycarbonyl)-4-oxo-8-sulfo-12-chloro-4H,6H-[2]-benzopyrano-[3,4-f]-[1]-benzopyran by method B A solution of 7.0 gm (0.022 mol) of 2-chloro-6H-dibenzo-[b,d]-pyranyl-(3)-fumaric acid ether in concentrated sulfuric acid (see Example 9) was stirred for 2 hours at room temperature. The dark reaction mixture was then poured into ice water, and the resulting precipitate, consisting mainly of 2-carboxy-4-oxo-12-chloro-4H,6H-[2]-benzopyrano-[3,4-f][1]-benzopyran, was filtered off. The aqueous phase was extracted with n-butanol, and the obtained solution was evaporated to dryness. After addition of ether, 2.5 gm (23.8% of theory) of the compound named in the heading, m.p. 95°–97° C, were obtained (contained 3 mols of water of crystallization).

EXAMPLE 11

2-(n-Butoxycarbonyl)-4-oxo-6,6-dimethyl-8-sulfo-12-chloro-4H,6H-[2]-benzopyrano-[3,4-f]-[1]-benzopyran by method B A solution of 18 gm (0.069 mol) of 2-chloro-3-hydroxy-6,6-dimethyl-6H-dibenzo-[b,d]-pyran (see Example 6) and 11.4 gm (0.8 mol) of dimethyl acetylene-dicarboxylate in 30 ml of dioxane was admixed with 1 ml of a 40% solution of benzyl trimethylammonium hydroxide in water, and the mixed solution was heated for 30 minutes at 80° C. After cooling, 50 ml of 5 N sodium hydroxide were added thereto, and the mixture was heated for 1 hour more. Then, the mixture was cooled, acidified with concentrated hydrochloric acid, extracted with ether, the extract was dried, the ether was evaporated, and the residue was poured into concentrated sulfuric acid. After standing for one day at room temperature, the solution was poured into ice water, and the precipitate formed thereby was filtered off. The aqueous phase was extracted with n-butanol, the solvent was evaporated from the extract to dryness, and the residue was recrystallized from ether. 3.5 gm (10% of theory) of the compound named in the heading, m.p. 241°–243° C, were obtained (with ½ mol of water of crystallization).

EXAMPLE 12

2-Carboxy-4-oxo-6,6-dimethyl-8-chloro-4H,6H-[2]-benzopyrano-[3,4-f]-[1]-benzopyran by method A A stirred solution of 6.0 gm (0.25 mol) of sodium in 100 ml of ethanol was admixed at 50° C with a suspension of 8.0 gm (0.028 mol) of 3-hydroxy-4-acetyl-8-chloro-6,6-dimethyl-6H-dibenzo-[b,d]-pyran in a mixture of 7.6 gm (0.052 mol) of diethyl oxalate and 125 ml of ethanol. The resulting mixture was refluxed for 1 hour, then cooled to room temperature, and the precipitated raw reaction product was filtered off, washed with ether, dried and heated in a mixture of 70 ml of acetic acid and 26 ml of hydrochloric acid. Subsequently, the mixture was cooled, and the precipitate formed thereby was collected by suction filtration and recrystallized from methanol/chloroform, yielding 4.8 gm (51% of theory) of the compound named in the heading, m.p. 257°–258° C.

Its ethanolamine salt, m.p. 201°–202° C, was obtained in analogy to the method described in Example 1.

The starting compound, m.p. 106°–107° C, was prepared in analogy to the method described in Example 2 from 2-bromo5-chloro-benzoic acid and 2,6-dihydroxy acetophenone via 3-hydroxy-4-acetyl-6-oxo-8-chloro-6H-dibenzo-[b,d]-pyran (m.p. 215°–216° C).

EXAMPLE 13

2-Ethoxycarbonyl-4,6-dioxo-4H,6H-[2]-benzopyrano-[3,4-f]-[1]-benzopyran by method A A stirred solution of 1.3 gm (0.05 mol) of sodium in 30 ml of ethanol was admixed at 50° C with a suspension of 2.5 gm (0.01 mol) of 3-hydroxy-4-acetyl-6-oxo-6H-dibenzo-[b,d]pyran (see Example 7) in a mixture of 2.8 gm (0.02 mol) of diethyl oxalate and 30 ml of ethanol. The resulting mixture was refluxed for 1 hour, then cooled to room temperature, and the precipitated raw reaction product was filtered off and heated in a mixture of 100 ml of ethanol and 5 ml of concentrated hydrochloric acid. The precipitate thus formed was filtered off, washed with ether and recrystallized from methanol/chloroform, yielding 1.5 gm (43.5%) of the compound named in the heading, m.p. 292°–294° C (contained ½ mol of water of crystallization.

For the preparation of the ethanolamine salt, the ester obtained above (500 mgm = 0.0015 mol) was refluxed in a mixture of 20 ml of acetic acid and 10 ml of concentrated hydrochloric acid for 1 hour. The reaction mixture was then cooled, and the free acid was isolated (m.p. of acid: 276°–277° C; 308 mgm). The acid was suspended in 200 ml of acetonitrile, and after addition of 61 mgm (0.001 mol) of ethanolamine, 280 mgm (52% of theory) of the ethanolamine salt, m.p. 240°–242° C, were obtained.

EXAMPLE 14

2-Carboxy-4-oxo-6,6,11-trimethyl-4H,6H-[2]-benzopyrano-[3,4-f]-[1]-benzopyran by method A A solution of 1.2 gm (4.3 millimols) of 1-methyl-3-hydroxy-4-acetyl-6,6-dimethyl-6H-dibenzo-[b,d]-pyran and 1.2 gm (8.3 millimols) of diethyl oxalate in 10 ml of ethanol was poured at 40° C into a solution of 1.03 gm (45 millimols) of sodium in 20 ml of ethanol. The mixture was refluxed for 1 hour, cooled to 10° C and acidified with 2 N hydrochloric acid. The raw reaction product was extracted twice with 15 ml of ether each, the combined extracts were dried, and the solvent was evaporated. The orange residue was refluxed for 1¾hours in 18.2 ml of a mixture of acetic acid and hydrochloric acid (1.2 : 1), the reaction mixture was then cooled, and the precipitate formed thereby was recrystallized from ethanol. 1.1 gm (77% of theory) of the compound named in the heading, m.p. 231°–232° C, were obtained.

EXAMPLE 15

2-Carboxy-4-oxo-6,6-dimethyl-8,9,11-trimethoxy-4H,6H-[2]-benzopyrano-[3,4-f]-[1]-benzopyran by method A A solution of 800 mgm (2.22 millimols) of 1,8,9-trimethoxy-4-acetyl-3-hydroxy-6,6-dimethyl-6H-dibenzo-[b,d]-pyran and 627 mgm (4.3 millimols) of diethyl oxalate in 22 ml of ethanol was stirred at 40° C into a solution of 510 mgm (22 millimols) of sodium in 11 ml of ethanol. The mixture was refluxed for 45 minutes, then cooled, and the raw reaction product was filtered off and refluxed in a mixture of 6 ml of acetic acid and 4 ml of concentrated hydrochloric acid for 65 minutes. Then, the reaction mixture was diluted with an equal volume of water and extracted three times with 10 ml of a mixture of benzene and tetrahydrofuran (1:1). The extract was dried over sodium sulfate, evaporated to dryness, and the residue was recrystallized three times from methanol. 170 mgm (19% of theory) of the compound named in the heading were obtained as its hemihydrate, m.p. 263°–264° C.

EXAMPLE 16

2-Carboxy-4-oxo-6,6-dimethyl-8-sulfo-12-chloro-4H,6H-[2]-benzopyrano-[3,4-f]-[1]-benzopyran 1.0 gm (2 millimols) of 2-(n-butoxycarbonyl)-4-oxo-6,6-dimethyl-8-sulfo-12-chloro-4H,6H-[2]-benzopyrano-[3,4-f]-[1]-benzopyran (see Example 11) was heated for 1 hour in a mixture of 12 ml of acetic acid and 5 ml of concentrated hydrochloric acid. Then, the reaction mixture was evaporated to dryness, and the residue was recrystallized from methanol. 0.5 gm (53% of theory) of the compound named in the heading, m.p. 257°–259° C, was obtained (with 2 mols of water of crystallization).

EXAMPLE 17

2-Carboxy-4-oxo-6,6-dimethyl-8-nitro-12-chloro-4H,6H-[2]-benzopyrano-[3,4-f]-[1]-benzopyran 1.6 gm (4.5 millimols) of 2-carboxy-4-oxo-6,6-dimethyl-12-chloro-4H,6H-[2]-benzopyrano-[3,4-f]-[1]-benzopyran (see Example 6) were stirred for 24 hours in a mixture of 35 ml of acetic acid and 5 ml of fuming nitric acid. The yellow precipitate formed thereby was filtered off and recrystallized from methanol/acetone. 1.5 gm (83.3% of theory) of the compound named in the heading, m.p. 278°–279° C, were obtained.

Its ethanolamine salt, m.p. 216°–218° C, was obtained in analogy to the method described in Example 1.

EXAMPLE 18

2-Carboxy-4-oxo-6,6,12-trimethyl-8-sulfo-4H,6H-[2]-benzopyrano-[3,4-f]-[1]-benzopyran by method B A solution of 17 gm (0.07 mol) of 2,6,6-trimethyl3-hydroxy-6H-dibenzo-[b,d]-pyran and 14.2 gm (0.1 mol) of dimethyl acetylene-dicarboxylate in 40 ml of dioxane was admixed with a 40% solution of benzyl trimethylammonium hydroxide in water. The mixed solution was heated at 80° C for 30 minutes, cooled, admixed with 50 ml of 5 N sodium hydroxide and again heated for 1 hour at 80° C. Then, the reaction mixture was cooled, acidified with concentrated hydrochloric acid and extracted with ether. The ether extract was dried and evaporated, and the oily residue thus obtained was added slowly at room temperature to 150 ml of concentrated sulfuric acid. After standing for 1 day at room temperature, the solution was poured into ice water, and the precipitated solid substance was filtered off and heated for 3 hours in a mixture of 25 ml of acetic acid and 10 ml of concentrated hydrochloric acid. Subsequently, the mixture was evaporated to dryness, and the residue was recrystallized from methanol, yielding the compound named in the heading in the form of reddish crystals, m.p. 264°–266° C (hemihydrate).

EXAMPLE 19

2-(n-Octyloxycarbonyl)-4-oxo-6,6-dimethyl-8-chloro-4H,6H-[2]-benzopyrano-[3,4-f]-[1]-benzopyran 1.2 gm (3.4 millimols) of 2-carboxy-4-oxo-6,6-dimethyl-8-chloro-4H,6H-[2]-benzopyrano-3,4-f]-[1]-benzopyran (see Example 12) were heated for 15 minutes in a mixture of 20 ml of n-octanol and 1 ml of concentrated hydrochloric acid. After 30 minutes of standing, the reaction mixture was cooled to 0° C and the precipitate which had formed was filtered off and recrystallized from ether. 1.5 gm (95% of theory) of the compound named in the heading, m.p. 111°–113° C, were obtained.

EXAMPLE 20

2-Carboxy-4-oxo-6,6-dimethyl-9-chloro-4H,6H-[2]-benzopyrano[3,4-f]-[1]-benzopyran by method A A suspension of 5.5 gm (0.018 mol) of 3-hydroxy-4-acetyl-9-chloro-6,6-dimethyl-6H-dibenzo-[b,d]-pyran in a mixture of 4.4 gm (0.03 mol) of diethyl oxalate and 100 ml of ethanol was quickly stirred into a solution of 3.0 gm (0.13 mol) of sodium in 100 ml of ethanol at a temperature of 50° C. The resulting mixture was refluxed for 1 hour, cooled to room temperature, and the raw reaction product was filtered off, washed with ether, dried and then heated in a mixture of 40 ml of acetic acid and 16 ml of concentrated hydrochloric acid. After the reaction had gone to completion, the mixture was cooled, and the precipitate which had formed was crystallized from methanol/chloroform. 3.0 gm (46% of theory) of the compound named in the heading, m.p. 262°–264° C, were obtained.

Its ethanolamine salt, obtained in analogy to Example 1, had a melting point of 195°–197° C.

The starting compound, m.p. 125°–128° C, was obtained by the method described in Example 2 from 2-bromo-4-chlorobenzoic acid and 2,6-dihydroxyacetophenone via 3-hydroxy-4-acetyl-6-oxo-9-chloro-6H-dibenzo-[b,d]-pyran (m.p. 227°–230° C).

The compounds of the present invention, that is, those embraced by formula I above and their salts, have useful pharmacodynamic properties. More particularly, they exhibit antiallergic activity in warm-blooded animals, such as rats, and are therefore useful for the treatment of allergic asthma, hay fever, atopical dermatitides and other allergic conditions.

The antiallergic activity of the compounds of the instant invention was ascertained by the so-called PCA-test (passive cutaneous anaphylaxis test) and compared to the antiallergic activity of the known related compound 1,3-bis(2'-carboxy-chromon-5'-yloxy)-2-hydroxy-propane.

In this test the skin of adult laboratory rats is sensitized by means of intradermal injections of egg albumin/β-pertussis-antiserum of exponentially decreasing concentrations, i.e. undiluted, 1:3, 1:9, 1:27, etc. One day later the test animals are administered egg albumin in Evans' Blue solution i.v. By measuring the size of the blue-colored area of the skin, the PCA-titer is determined. The test compound is administered i.v. together with the Evans' Blue solution at varying concentrations. Each rat receives 5 mgm of egg albumin dissolved in 1 ml of a 0.25% Evans' Blue solution in a sterile salt solution. 25 to 30 minutes after administration of the dye and the test compound the animals are killed, and the area of blue coloration on the inside surface of the skin is measured in mm². The PCA-titer is the reciprocal value of that serum dilution at which a blue coloration with a diameter of at least 5 mm is just barely discernable. The reduction in the PCA-titer is a measure of the degree of suppression of allergic reactions, in the present case against albumin, produced by the test compound.

The following table shows the results obtained from this test for 2-carboxy-4-oxo-6,6dimethyl-11-methoxy-4H,6H-[2]-benzopyrano-[3,4-f]-[1]-benzopyran (I), which is representative of the genus embraced by formula I, in comparison to the known antiallergic 1,3-(2'-carboxy-chromon-5'-yloxy)-2-hydroxy-propane (II):

| Compound | % Reduction of P C A - titer | | | |
|---|---|---|---|---|
| | 0.5 mgm | 1.0 mgm | 5.0 mgm | 10.0 mgm (i.v.) |
| II | — | 20 | 60 | 89 |
| I | 50 | 83 | — | 92 |

These values clearly show that the compound of the instant invention is a significantly more effective antiallergic than the known compound.

For pharmaceutical purposes the compounds according to the present invention are administered to warm-blooded animals topically, perorally, parenterally or by the respiratory route as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, inhalation aerosols, emulsions, syrups, suppositories and the like. One effective parenteral or inhalation dosage unit of the compounds according to the present invention is from 0.083 to 0.84 mgm/kg body weight, and the peroral dosage range is from 0.83 to 8.4 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 21

Tablets

The tablet composition is compounded from the following ingredients:

| | | |
|---|---|---|
| Ethanolamine salt of 2-carboxy-4-oxo-6,6-dimethyl-11-methoxy-4H,6H-[2]-benzopyrano-[3,4-f]-[1]-benzopyran | 0.100 | parts |
| Stearic acid | 0.010 | '' |
| Dextrose | 1.890 | '' |
| Total | 2.000 | parts |

Preparation:

The ingredients are admixed in conventional manner, and the mixture is compressed into 2.0 gm-tablets, each of which contains 100 mgm of the benzopyrano-benzopyran salt and is an oral dosage unit composition with effective antiallergic action.

EXAMPLE 22

Ointment

The ointment composition is compounded from the following ingredients:

| | | | |
|---|---|---|---|
| Ethanolamine salt of 2-caboxy-4-oxo-6,6-dimethyl-11-methoxy-4H,6H[2]-benzopyrano-[3,4-f]-[1]-benzopyran | | 2.000 | parts |
| Fuming hydrochloric acid | | 0.011 | '' |
| Sodium pyrosulfite | | 0.050 | '' |
| Mixture (1:1) of cetyl alcohol and stearyl alcohol | | 20.000 | '' |
| White vaseline | | 5.000 | '' |
| Synthetic bergamot oil | | 0.075 | '' |
| Distilled water | q.s.ad | 100.000 | '' |

Preparation:

The ingredients are uniformly blended in conventional manner into an ointment, 100 gm of which contain 2.0 gm of the benzopyrano-benzopyran salt. The ointment is an effective antiallergic composition for topical application.

EXAMPLE 23

Inhalation aerosol

The aerosol composition is compounded from the following ingredients:

| | | |
|---|---|---|
| Ethanolamine salt of 2-carboxy-4-oxo-6,6-dimethyl-11-methoxy-4H,6H-[2]-benzopyrano-[3,4-f]-[1]-benzopyran | 1.00 | parts |
| Soybean lecithin | 0.20 | '' |
| Propellent gas mixture (frigen 11, | | |

-continued

| | | |
|---|---|---|
| 12 and 14) | q.s.ad | 100.00 " |

Preparation:

The ingredients are compounded in conventional manner, and the composition is filled into aerosol containers with a metering valve which releases 5 to 20 mgm of active ingredient per actuation of the valve. The aerosol spray is a dosage unit composition with effective antiallergic action for administration by the respiratory route.

EXAMPLE 24

Hypodermic solution

The solution is compounded from the following ingredients:

| | | |
|---|---|---|
| Ethanolamine salt of 2-carboxy-4-oxo-6,6-dimethyl-11-methoxy-4H,6H-[2]-benzo-pyrano-[3,4-f]-[1]-benzopyran | 50.0 | parts |
| Sodium pyrosulfite | 1.0 | " |
| Sodium salt of EDTA | 0.5 | " |
| Sodium chloride | 8.5 | " |
| Double-distilled water | q.s.ad 1000.0 | " |

Preparation:

The individual ingredients are dissolved in a sufficient amount of double-distilled water, the solution is diluted to the indicated concentration with additional double-distilled water, the resulting solution is filtered until free from suspended particles, and the filtrate is filled under aseptic conditions into 1 ml-ampules which are subsequently sterilized and sealed. Each ampule contains 50 mgm of the benzopyrano-benzopyran salt, and the contents thereof are an injectable dosage unit composition with effective anti-allergic action.

Analogous results are obtained when any one of the other benzopyrano-benzopyrans embraced by formula I or a salt thereof is substituted for the particular active ingredient in Examples 21 through 24. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula wherein the
$R_1$'s are hydrogen, alkyl of 1 to 3 carbon atoms or together a double-bonded oxygen,
$R_2$ is hydrogen, fluorine, chlorine, methyl, hydroxyl, methoxy, hydroxy-ethoxy, nitro or $-SO_3H$,
$R_3$ is hydrogen, fluorine, chlorine or methoxy,
$R_4$ is hydrogen, methyl or methoxy,
$R_5$ is hydrogen, fluorine, chlorine or methyl, and
$R_6$ is hydrogen or alkyl of 1 to 8 carbon atoms, or, when $R_6$ is hydrogen, a pharmaceutical salt thereof formed with an inorganic or organic base.

2. A compound of claim 1, which is 2-carboxy-4-oxo-6,6-dimethyl-11-methoxy-4H,6H-[2]-benzopyrano-[3,4-f]-[1]-benzopyran or a pharmaceutical salt thereof formed with an inorganic or organic base.

3. An antiallergic pharmaceutical dosage unit composition consisting essentially of an inert pharmaceutical carrier and an effective antiallergic amount of a compound of claim 1.

4. The method of suppressing allergic reactions in a warm-blooded animal, which comprises administering to said animal an effective antiallergic amount of a compound of claim 1.

* * * * *